(12) United States Patent
Peyman

(10) Patent No.: US 7,354,574 B2
(45) Date of Patent: Apr. 8, 2008

(54) TREATMENT OF OCULAR DISEASE

(75) Inventor: Gholam A. Peyman, New Orleans, LA (US)

(73) Assignee: Advanced Ocular Systems Limited, Nedlands (AU)

( * ) Notice: Subject to any disclaimer, the term of this patent is extended or adjusted under 35 U.S.C. 154(b) by 0 days.

(21) Appl. No.: 10/289,772

(22) Filed: Nov. 7, 2002

(65) Prior Publication Data

US 2004/0092435 A1    May 13, 2004

(51) Int. Cl.
*A61K 31/74*    (2006.01)
*A61K 38/16*    (2006.01)

(52) U.S. Cl. ................... 424/78.04; 514/11; 514/954

(58) Field of Classification Search ............... 424/486, 424/484, 78.04; 514/11, 912, 866, 566
See application file for complete search history.

(56) References Cited

U.S. PATENT DOCUMENTS

| | | | |
|---|---|---|---|
| 4,079,038 A | 3/1978 | Choi et al. | |
| 4,093,709 A | 6/1978 | Choi et al. | |
| 4,131,648 A | 12/1978 | Choi et al. | |
| 4,138,344 A | 2/1979 | Choi et al. | |
| 4,180,646 A | 12/1979 | Choi et al. | |
| 4,304,767 A | 12/1981 | Heller et al. | |
| 4,946,931 A | 8/1990 | Heller et al. | |
| 5,294,604 A | 3/1994 | Nussenblatt et al. | |
| 5,387,589 A | 2/1995 | Kulkarni | |
| 5,411,952 A | 5/1995 | Kaswan | |
| 5,457,182 A | 10/1995 | Wiederrecht et al. | |
| 5,770,607 A | 6/1998 | Honbo et al. | |
| 5,773,019 A * | 6/1998 | Ashton et al. | |
| 5,952,371 A | 9/1999 | Baker et al. | |
| 5,968,543 A | 10/1999 | Heller et al. | |
| 6,004,565 A | 12/1999 | Chiba et al. | |
| 6,179,817 B1 | 1/2001 | Zhong | |
| 6,238,799 B1 | 5/2001 | Opolski | |
| 6,239,113 B1 | 5/2001 | Dawson et al. | |
| 6,258,856 B1 | 7/2001 | Chanberlain et al. | |
| 6,306,422 B1 | 10/2001 | Batich et al. | |
| 6,331,313 B1 | 12/2001 | Wong et al. | |
| 6,350,442 B2 | 2/2002 | Garst | |
| 6,413,536 B1 | 7/2002 | Gibson et al. | |
| 6,436,906 B1 | 8/2002 | Or et al. | |
| 6,440,942 B1 | 8/2002 | Or et al. | |
| 6,462,026 B1 | 10/2002 | Or et al. | |
| 6,462,071 B1 * | 10/2002 | Castillejos | |
| 6,482,799 B1 | 11/2002 | Tuse et al. | |
| 6,489,335 B2 | 12/2002 | Oeyman | |
| 6,534,693 B2 | 3/2003 | Fischell et al. | |
| 6,596,296 B1 | 7/2003 | Nelson et al. | |
| 6,613,355 B2 | 9/2003 | Ng et al. | |
| 6,617,345 B1 | 9/2003 | Gregory et al. | |
| 6,667,371 B2 | 12/2003 | Ng et al. | |
| 6,670,398 B2 | 12/2003 | Edwards et al. | |
| 6,673,807 B1 * | 1/2004 | Sakai et al. | |
| 6,713,081 B2 * | 3/2004 | Robinson et al. | |
| 6,864,232 B1 | 3/2005 | Ueno | |
| 6,872,383 B2 | 3/2005 | Ueno | |
| 2002/0015957 A1 | 2/2002 | Hageman et al. | |
| 2002/0187998 A1 | 12/2002 | Ueno | |
| 2003/0018044 A1 | 1/2003 | Peyman | |
| 2003/0044452 A1 | 3/2003 | Ueno | |
| 2003/0069232 A1 | 4/2003 | Chiou | |
| 2003/0130301 A1 | 7/2003 | Ueno | |
| 2004/0092435 A1 | 5/2004 | Peyman | |
| 2004/0198763 A1 | 10/2004 | Ueno | |
| 2005/0025810 A1 | 2/2005 | Peyman | |
| 2005/0063996 A1 | 3/2005 | Peyman | |
| 2005/0063997 A1 | 3/2005 | Peyman | |
| 2005/0064010 A1 | 3/2005 | Cooper et al. | |
| 2005/0070468 A1 | 3/2005 | Ueno | |

FOREIGN PATENT DOCUMENTS

| | | |
|---|---|---|
| AU | 17386/88 | 10/1988 |
| AU | 2350/92 | 7/1992 |
| CN | 1333018 | 1/2002 |
| CN | 1340358 | 3/2002 |
| CN | 1456350 | 11/2003 |
| DE | 19810655 | 9/1999 |
| EP | 1 074 255 | 2/2001 |
| EP | 107425 | 2/2001 |
| EP | 1142566 | 10/2001 |

(Continued)

OTHER PUBLICATIONS

Cicciarell et al., IOVS (Mar. 15, 2001), 42(4): S332. Pharmacokinetics of subconjunctivally administered cyclosporine A. Local delivery prior to chemotherapy for retinoblastoma.*

Grisolano et al., Ophthalmic Surgery (1986), 17:155-156. Retinal toxicity study of intravitreal cyclosporin.*

Lai et al., IOVS (Sep. 2000), 41(10): 3134-3141. Local immunosuppression prolongs survival of RPE xenografts labeled by retroviral gene transfer.*

Shen et al., Archives of Ophthalmology (Jul. 2001), 119(7): 1033-1043. Combined effect of cyclosporine and sirolimus on improving the longevity of recombinant adenovirus-mediated transgene expression in the retina.*

Wakelee-Lynch, Diabetes Care (1992), 15(2):300-301. Interferon may offer first drug therapy for diabetic retinopathy.*

(Continued)

*Primary Examiner*—Michele Flood
(74) *Attorney, Agent, or Firm*—Frommer Lawrence & Haug LLP; Thomas J. Kowalski; Ann-Marie C. Yvon

(57) ABSTRACT

A method and article to treat ocular disease with Cyclosporin A alone or with compounds related to Cyclosporin A for intraocular injection or implantation. Treatment does not result in ocular toxicity and encompasses age related macular degeneration, retinitis pigmentosa, and retinopathy such as diabetic retinopathy.

11 Claims, No Drawings

FOREIGN PATENT DOCUMENTS

| | | |
|---|---|---|
| EP | 0532 862 | 3/2003 |
| JP | 07010752 | 1/1995 |
| JP | 1997030966 A | 2/1997 |
| JP | 09315954 | 12/1997 |
| JP | 10-218787 | 8/1998 |
| JP | 2001-064198 | 3/2001 |
| WO | WO/89/01772 | 3/1989 |
| WO | WO 99/22722 | 5/1999 |
| WO | WO 99/34830 | 7/1999 |
| WO | WO 99/42104 | 8/1999 |
| WO | WO 00/66122 | 11/2000 |
| WO | WO 02/24234 | 3/2002 |
| WO | WO 02085928 | 10/2002 |
| WO | WO 03/017990 | 3/2003 |
| WO | WO 03/051385 | 6/2003 |
| WO | WO 2004/014373 | 2/2004 |
| WO | WO 2004/027027 | 4/2004 |
| WO | WO 2004/043480 | 5/2004 |
| WO | WO 2004/096261 | 11/2004 |
| WO | WO 2005/011813 | 2/2005 |
| WO | WO 2005/027906 | 3/2005 |
| WO | WO 2005/030205 | 4/2005 |

OTHER PUBLICATIONS

Peyman et al., Japanense Journal of Ophthalmology (1989), 33(4): 392-404. Intravitreal drug therapy.*
Peyman et al., Intravitreal Surgery: Principles and Practice, 2nd Edition, 1994. Appleton & Lange, Connecticut, pp. 443-452.*
Peyman et al., Intravitreal Surgery: Principles and Practice, 2nd Edition, 1994. Appleton & Lange, Connecticut, pp. 443-452.*
Grisolano et al.. Ophthalmic Surgery (1986), 17: 155-156. Retinal toxicity study of intravitreal cylcosporine.*
U1, Carmo et al., Mediators of Inflammation (2000), 9(5): 243-248. Effect of cyclosporin A on the blood-retinal barrier permeability in streptozotocin-induced diabetes.*
V1, Karacorlu et al., Ophthalmic Surgery (1999), 23:833-835. Lack of toxicity of intravitreally administered interferon Alpha-2a.*
W1, Stosic-Grujicic et al., Clinical & Experimental Immunology (1999), 117(1):44-50. Leflunomide protects mice from multiple low dose streptozotocin (MLD-SA)- induced insulitis and diabetes.*
X1, Nicoletti et al., Scandainavian Journal of Immunology (1992), 36(3): 415-420. The effects of deoxyspergualin on the developmentn of diabetes in diabetes-prone BB rats.*
U2, Lai et al., IOVS (Sep. 2000), 41(10): 3134-3141. Local immunosuppression prolongs survival of RPE xenografts labeled by retroviral gene transfer.*
V2, Shen et al., Archives of Ophthalmology (Jul. 2001), 119(7): 1033-1043. Combined effect of cyclosporine and sirolimus on improving the longevity of recombinant adenovirus-mediated transgene expression in the retina.*
Algvere, P.V. et al., European J of Ophthalomology (1999), 9(3): 217-230. Long-term outcome of RPE allografts in non-immunosuppressed patients with AMD.*
Del Cerro, M. et al. Invest. Ophthalmology & Visual Science (2000), 41(10): 3142-8. Histologic correlation of human neural retinal transplantation.*
Lopez, R. et al. Invest. Ophthalmology & Visual Science (1989), 30: 586-588. Transplanted retinal pigment epithelium modifies the retinal degeneration in the RCS.*
Das et al., Experimental Neurology (1999), 157: 58-68. The transplantation of human fetal neuroretinal cells in advanced retinitis pigmentosa patients: Results of a long-term safety study.*
Aramant, R.B. et al. Science & Medicines (2000), 7: 20-29. Retinal transplantation.*
Lund, R.D. et al. PNCS (2001), 98(17): 9942-9947. Subretinal transplantation of genetically modified human cell lines attenuates loss of visual function in dystrophic rats.*
Jiang, L.Q. et al. Investigative Ophthalmology & Visual Science (1994), 35(13): 4300-4308. Corneal electroretinographic function rescued by normal retinal pigment epithelial grafts in retinal degenerative Royal College of Surgeons rats.*
V4, Shen et al., Archives of Ophthalmology (Jul. 2001), 119(7): 1033-1043. Combined effect of cyclosporine and sirolimus on improving the longevity of recombinant adenovirus-mediated transgene expression in the retina.*
Carmo et al., Mediators of Inflammation (2000), 9(5): 243-248. Effect of cyclosporin A on the blood-retinal barrier permeability in streptozotocin-induced diabetes.*
Elke Passos, MD, et al.,, *Ocular Toxicity of Intravitreal Tacrolimus.*, Ophthalmic Surgery and Lasers, Mar./Apr. 2002, vol. 33, No. 2, pp. 140-144.
Gholam A. Peyman, MD, et al., *Implanation of a sustained-release ganciclovir implant.*, Virtreoretinal Surgical Techniques, Martin Dunitz Ltd., 2001, Chapter 45, pp. 521-531.
Graeme M. Lipper, et al.,, *Recent therapeutic advances in dermatology*, JAMA, vol. 283, No. 2, Jan. 12, 2000, pp. 175-177.
Eric D. Donnenfeld, et al.,, *Cyclosporine provides effective treatment for dry eye.*, therapeutic Updates in Ophthalmology, Special Issue, Jul. 1999, pp. 1-3.
Maxine Lipner,, *Dry Eye 101: Developing etiologies and treatments for this widespread syndrome,*, EyeWorld, Feb. 1999, pp. 19ff.
Jeffrey P. Gilbard,, *EW Interview: Electrolyte balance is key to dry-eye product's success,*, EyeWorld, Feb. 1999, pp. 20ff.
Gholam A. Peyman, et al.,, *Keratitis (Noninfectious).*, Principles and Practice of Ophthalmology, W.B. Saunders Company, 1980, pp. 446-449.
Don H. Anderson, Ph.D., et al.,, *A role for Local Inflammation in the Formation of Drusen in the Aging Eye.*, American Journal of Ophthalmology, vol. 134, No. 3, Sep. 2002, pp. 411-431.
Enyedi, L.B. et al., *An intravitreal device providing sustained release of cyclosporine and dexamethasone*, Current Eye Research, May 1996, vol. 15, No. 5, pp. 549-557.
Enyedi, L.B. et al., *Pharmacokinetics and toxicity of an intravitreal device providing sustained release of cyclosporine (CsA) and dexamethasone (DEX)*, Investigative Ophthalmology and Visual Science, vol. 35, No. 4, 1994, p. 1906, and Annual Meeting of the Association for Research in Vision and Ophthalmology, Sarasota, FL, USA, May 1-6, 1994 abstract.
Apel, A., et al., *A subconjunctival degradable implant for cyclosporine delivery in corneal transplant therapy*, Current Eye Research, vol. 14, No. 8, Aug. 1995, pp. 659-667.
Garweg, J. et al., *Therapy of Goldmann-Favre's Vitreo-Retinal Degeneration with Cyclosporin A and Bromocriptine*, Klinische Monatsblatter fur Augenheilkunde, vol. 199, No. 3, Sep. 1991, pp. 199-205.
Lallemand, F. et al., *Cyclosporine A delivery to the eye: A pharmaceutical challenge*, European Journal of Pharmaceutics and Biopharmaceutics, 56 (2003), pp. 307-318.
PCT, *International Search Report*, PCT/US03/28315, mailed Jun. 15, 2004, 6 pages.
Grisolano et al., *Retinal Toxicity Study of Intravitreal Cyclosporin*, Ophthalmic Surgery, Mar. 1986, 17:155-156.
Kiryu et al., *In Vivo Evaluation of the Inhibitory Effects of Tacrolimus (FK506) on Leukocyte Accumulation During Retinal Ischemia Reperfusion Injury*, ARVO 1998 Meeting, Ft. Lauderdale, FL, Poster Presentation 1247-B128.
Martin, DF et al., *Synergistic Effect of Rapamycin and Cyclosporin A in the Treatment of Experimental Autoimmune Uveoretinitis*, The Journal of Immunology, 1995, 154:922-927.
Apel et al., *A subconjunctival degradable implant for cyclosporine delivery in corneal transplant therapy*, Curr. Eye Res. 14:659-667, 1995.
Aron-Rosa, *Pulsed Nd:YAG lasers in opthalmology*, Nd:YAG Laser Applications pp. 34-48.
Costantini et al., *Immunophilin Ligands and GDNF Enhance Neurite Branching or Elongation from Developing Dopamine Neurons in Culture*, Experimental Neurology 164, 60-70 (2000).
Dewey, *2003 PCO Update: Part 1—How the square-edged IOL prevents posterior capsular opacification*, Cataract & Refractive Surgery Today, Sep. 2003, pp. 20-22.
Goodman & Gilman, *The Pharmacological Basis of Therapeutics, 8th Ed.*, Pergamon Press, New York, 1990, pp. 1024-1033.

Keep et al, *Immunosuppressants, Neurologic Disorders, and Neuroprotection*, Chapter I, Immunosuppressant Analogs in Neuroprotection, Borlongan et al Eds., 2002, Humana Press, Totowa NJ, pp. 3-32.

PCT, *International Search Report*, PCT/2004/024054, filed Jul. 27, 2004, 7 pg.

Peyman et al., *Vitreoretinal Surgical Techniques*, Martin Dunitz, London, 2001, Chapter 45, pp. 521-531.

Peyman, *Pupillary Membranes: Nd:YAG Capsulotomy*, Intravitreal Surgery, Norwalk CT, Appleton & Lange, 1994, pp. 253-257.

Revill et al., *Genetically Engineered Analogs of Ascomycin for Nerve Regeneration*, Journal of Pharmacology and Experimental Therapeutics, vol. 302:1278-1285 (2002).

Schonfield and Kirst, *Macrolide Antibiotics*, Birkhausen, Basil, Switzerland, 2002, pp. 1-36.

Wise, *Handbook of Pharmaceutical Controlled Release Technology*, Marcel Dekker, New York, 2000.

* cited by examiner

TREATMENT OF OCULAR DISEASE

FIELD OF THE INVENTION

The invention is directed to therapeutic treatment of age-related macular degeneration, retinitis pigmentosa, and diabetic retinopathy with Cyclosporin A.

BACKGROUND

The immunomodulator Cyclosporin A (cyclosporine, topical formulation Arrestase®, Allergan Inc.) has been used to treat glaucoma, corticosteroid-induced ocular hypertension, allograft rejection, infections, and ocular surface disease. Its use has been reported for the treatment of uveitis (inflammation of the uvea) by topical, intravitreal or systemic administration with doses of 0.05%, 0.1%, and 0.5%. Cyclosporin A has good penetration into the cornea but not into the anterior chamber, and does not increase intraocular pressure or cause cataracts. Its known toxicity had previously limited its use for other ocular diseases.

SUMMARY OF THE INVENTION

A method of treating age-related macular degeneration, retinitis pigmentosa, and diabetic retinopathy in the absence of substantial toxicity by administering Cyclosporin A in an effective amount and in a pharmaceutically acceptable formulation. "Treating" includes preventing progression of pre-existing disease, delaying onset and/or severity of disease, and ameliorating or reducing the severity, frequency, duration, etc., of one or more symptoms of disease.

In one embodiment, Cyclosporin A is injected intraocularly, for example by subconjuctival, intravitreal, subretinal, or retrobulbar injection. For subconjctival injection, a concentration in the range of about 1 ng/ml to about 500 µg/ml may be used. For intravitreal injection, a concentration in the range of about 1 µg/0.1 ml to about 1000 µg/0.1 ml may be used; one concentration that may be used is about 50 µg/0.1 ml. For subretinal injection, a concentration in the range of about 1 µg/0.1 ml to about 100 µg/0.1 ml may be used. For retrobulbar injection, a concentration in the range of about 20 µg/ml to about 1000 µg/ml may be used. Cyclosporin A may be administered in an aqueous-based solution, for example, bound to liposomes, or it may be dissolved in an organic solvent. In another alternative embodiment, Cyclosporin A may also be provided in an inert physiologically acceptable carrier such as a microsphere, liposome, capsule or polymeric matrix by injection or by surgical implantation in the eye or on the eye. Aqueous solvents that may be used include, but are not limited to, 0.9% saline and 5% dextrose. Organic solvents that may be used include, but are not limited to, dimethylsulfoxide (DMSO) or an alcohol. An implant may provide a time-release form of Cyclosporin A to achieve a constant dose of drug.

A method is also disclosed to reduce the onset or progression of diabetic retinopathy, age-related macular degeneration and/or retinitis pigmentosa, by intraocularly administering a composition containing Cyclosporin A, either alone or with other compounds that are related to Cyclosporin A, as the active agent in a pharmaceutically acceptable formulation and in an effective amount without causing substantial toxicity. The composition may contain Cyclosporin A as the sole active agent, the other agents being those that do not materially affect the basic properties of Cyclosporin A. Alternatively, the composition may contain other active agents, such as tacrolimus, besides Cyclosporin A. The composition may be injected or implanted in the eye.

The invention encompasses a method to treat a patient by intraocularly administering a composition containing Cyclosporin A as the active agent in a pharmaceutically acceptable formulation and in an amount effective to treat macular degeneration, retinopathy, or retinitis pigmentosa without substantial ocular toxicity. The composition is injected or implanted in the eye, and may be administered in a time-release formulation.

A sustained release formulation, such as a matrix, may be loaded with an amount of Cyclosporin A that would be toxic if released at a non-controlled rate, or a supratherapeutic amount, but which is formulated to release a non-toxic therapeutic amount of Cyclosporin A over a period of time. For example, a matrix may contain at least about 1 mg Cyclosporin A and may sustainedly release a non-toxic maintenance dose of Cyclosporin A. Such a matrix may be a diffusible walled reservoir and may be lipid, polyvinyl alcohol, polyvinyl acetate, polycaprolactone, poly(glycolic) acid, and/or poly(lactic)acid.

The invention will further be appreciated with respect to the following detailed description.

DETAILED DESCRIPTION

Cyclosporin A is a cyclic peptide produced by *Trichoderma polysporum*. It is available commercially, for example, from Sigma Chemicals (St. Louis, Mo.). It is an immunosuppressant and acts in a particular subset of T lymphocytes, the helper T cells. Cyclosporin A exerts an immunosuppressant effect by inhibiting production of the cytokine interleukin 2. Each of Cyclosporin A and tacrolimus, another immunosuppressant, produce significant renal and hepatic toxicity when each is administered systemically; because of this toxicity, they are not administered together.

Direct intraocular injection of 200 µg Cyclosporin A or less is non-toxic. Ocular toxicity may manifest as a gross and/or histologic retinal and/or vitreous toxic reaction. Evidence of such a toxic reaction may include one or more of white vitreous bodies, white vitreous opacities, electroretinography abnormalities such as reduction in mean B-wave amplitude in both scotopic and photopic conditions, occlusion of the temporal retinal vessels, and fibrin deposits.

Cyclosporin A may be administered intraacularly in a composition in which it is the only active agent. Alternatively, Cyclosporin A may be administered intraocularly in a composition with related compounds. Related compounds are other immunosuppressants that include, but are not limited to, tacrolimus, cyclophosphamide, sirolimus, atoposide, thiotepa, methotrexate, azathioprine (imuran), interferons, infliximab, etanercept, mycophenolate mofetil, 15-deoxyspergualin, thalidomide, glatiramer, leflunomide, vincristine, cytarabine, etc.

Cyclosporin A may be administered intraocularly in a composition in which it is the only active agent. Alternatively, Cyclosporin A may be administered intraocularly in a composition with related compounds. Related compounds are other immunosuppressants that include, but are not limited to, tacrolimus, cyclophosphamide, sirolimus, atoposide, thioepa, methotrexate, azathioprine (imuran), interferons, infliximab, etanercept, mycophenolate mofetil, 15-deoxyspergualin, thalidomide, glatiramer, leflunomide, vincristine, cytarabine, etc.

In one embodiment, the composition containing Cyclosporin A is administered in an amount or at a dose that does not result in substantial toxicity to the eye. As used herein, a lack of substantial toxicity encompasses both the absence of any manifestations of toxicity, as well as manifestations of toxicity which one skilled in the art would consider not sufficiently detrimental to decrease or cease treatment. As one example, fibrin deposits may be present indicating some toxicity, but less than substantial toxicity if their duration, number, etc., does not warrant that treatment be curtailed or stopped. As another example, white vitreous bodies and fibrin bodies may be present indicating some toxicity, but less than substantial toxicity if their duration, number, etc., does not warrant that treatment be curtailed or stopped.

Direct intraocular injection of a dose up to about 200 µg Cyclosporin A occurs without substantial toxicity to the patient. The intravenous solution form of Cyclosporin A may be diluted to achieve the indicated concentration using 0.9% NaCl or 5% dextrose, or an organic solvent such as dimethylsulfoxide (DMSO) or alcohol. Intraocular administration may be by any of the routes and formulations previously described. For injection, either a solution, emulsion, suspension, capsular formulation of microspheres or liposomes, etc. may be used.

Cyclosporin A may be administered surgically as an ocular implant. As one example, a reservoir container having a diffusible wall of polyvinyl alcohol or polyvinyl acetate and containing milligram quantities of Cyclosporin A may be implanted in or on the sclera. As another example, Cyclosporin A in milligram quantities may be incorporated into a polymeric matrix having dimensions of about 2 mm by 4 mm, and made of a polymer such as polycaprolactone, poly(glycolic) acid, poly(lactic) acid, or a polyanhydride, or a lipid such as sebacic acid, and may be implanted on the sclera or in the eye. This is usually accomplished with the patient receiving either a topical or local anesthetic and using a small (3-4 mm incision) made behind the cornea. The matrix, containing Cyclosporin A, is then inserted through the incision and sutured to the sclera using 9-0 nylon.

Cyclosporin A may be contained within an inert matrix for injection into the eye. As one example of an inert matrix, liposomes may be prepared from dipalmitoyl phosphatidylcholine (DPPC), such as egg phosphatidylcholine (PC), a lipid having a low heat transition. Liposomes are made using standard procedures as known to one skilled in the art. Cyclosporin A, in amounts ranging from nanogram to microgram to milligram quantities, is added to a solution of egg PC, and the lipophilic drug binds to the liposome.

A time-release drug delivery system may be implanted intraocularly to result in sustained release of the active agent over a period of time. The implantable structure may be in the form of a capsule of any of the polymers previously disclosed (e.g., polycaprolactone, poly(glycolic) acid, poly (lactic) acid, polyanhydride) or lipids that may be formulation as microspheres. As an illustrative example, Cyclosporin A may be mixed with polyvinyl alcohol (PVA), the mixture then dried and coated with ethylene vinyl acetate, then cooled again with PVA. In a formulation for intraocular injection, the liposome capsule degrades due to cellular digestion and can be a slow release drug delivery system, allowing the patient a constant exposure to the drug over time.

In a time-release formulation, the microsphere, capsule, liposome, etc. may contain a concentration of Cyclosporin A that could be toxic if it were administered as a bolus dose. The time-release administration, however, is formulated so that the concentration released over any period of time does not exceed a toxic amount. This is accomplished, for example, through various formulations of the vehicle (coated or uncoated microsphere, coated or uncoated capsule, lipid or polymer components, unilamellar or multilamellar structure, and combinations of the above, etc.). Other variables may include the patient's pharmacokinetic-pharmacodynamic parameters (e.g., body mass, gender, plasma clearance rate, hepatic function, etc.).

Depending upon the amount of Cyclosporin A provided in the formulation, a patient could be dosed over a period of years from a single implant or injection. As illustrative but non-limiting examples, a capsule can be loaded with 1-2 mg of Cyclosporin A; if the capsule is formulated to release a few micrograms of drug per day, the patient could be dosed for about 1000 days, or almost three years. As another example, If the capsule is loaded with 5 mg of drug, the patient could be dosed for about fifteen years. Such a formulation provides benefits which include accurate dosing with heightened patient convenience, because intervention is required in some cases only once or twice a decade or even less frequently.

The formation and loading of microspheres, microcapsules, liposomes, etc. and their ocular implantation are standard techniques known by one skilled in the art, for example, the use a ganciclovir sustained-release implant to treat cytomegalovirus retinitis, disclosed in Vitreoretinal Surgical Techniques, Peyman et al., Eds. (Martin Dunitz. London 2001, chapter 45); Handbook of Pharmaceutical Controlled Release Technology, Wise, Ed. (Marcel Dekker, New York 2000), the relevant sections of which are incorporated by reference herein in their entirety.

Cyclosporin A, either alone or in combination with other agents, may be administered intraocularly and without substantial toxicity, to treat retinopathy such as occurs in diabetic patients, macular degeneration, and retinitis pigmentosa, using the methods and formulations previously described. As described, this may be achieved by one or a combination of factors, such as by slowing disease progression, lessening its severity, lengthening the time of onset, etc.

Diabetic retinopathy is a leading cause of blindness. Patients with diabetes mellitus have an absolute or relative lack of circulating insulin and, through a variety of factors, frequently present with vascular changes in the retina. These changes manifest in retinal microaneurysms, small hemorrhages, and exudates, and lead to the formation of scar tissue. New blood vessels may form around the optic disk (proliferative retinopathy). Overtime, the cumulative results of such vascular effects lead to ocular pathologies which, ultimately, decrease vision in the diabetic patient. Thus, compositions and methods which reduce these vascular changes, or reduce their effects, improve the chances of a diabetic patient either maintaining vision, or at least slowing loss of vision.

Macular degeneration, also called age-related macular degeneration is a pathological condition that results in proliferation of new blood vessels in the subretinal area. While the presence of the new vessels themselves is not problematic, the new vessels leak blood and other serous fluid which accumulate in surrounding spaces. It is this fluid accumulation that leads to visual impairment. For example, in the retina, both the large vessels and the capillaries normally have intact vessel walls. In the choroid, the large vessels normally have intact vessel walls, but the capillary walls or membranes contain fenestrations or openings. Any endogenous or exogenous fluid present in these capillaries, for example, blood, serous fluid, solubilized drug, etc. will leak outside the vessels and into the surrounding area. The accumulation of fluid can result in serous and hemorrhagic detachment of the retinal pigment epithelium and neurosensory retina, and can lead to loss of vision due to fibrous deform scarring. Patients with an early stage of age-related macular degeneration can be diagnosed by the presence in the eye of abnormal clumps of pigments, termed drusen, which are dead outer segments of photoreceptor cells under the retinal pigment epithelium. The presence of large, soft drusen in the eye indicates a pre-stage of exudative age-related macular degeneration, and places these patients at higher-than-average risk for developing neovascularizations, especially if one eye is already affected.

Retinitis pigmentosa is a general term that encompasses a disparate group of disorders of rods and cones, which are the sensory structures in the retina. While retinitis pigmentosa is a genetic disorder, and is not an inflammatory process, one manifestation of the disease is the presence of irregular black deposits of clumped pigment in the peripheral retina. Thus, there is likely at least some immune component to retinitis pigmentosa.

While not being bound by a specific theory or mechanism, it is possible that the therapeutic efficacy of Cyclosporin A may involve its immunosuppressant activity. For example, diabetic patients treated with immunosuppressant drugs for reasons unrelated to vision develop less retinopathy over time than other diabetic patients. As another example, the drusen that is present in age-related macular degeneration constitutes a chronic inflammatory stimulus that becomes the target for encapsulation by a variety of inflammatory mediators, such as compliment. Treatment with immunosuppressant drugs may ameliorate this reaction. Immunosuppressant therapy results in decreased numbers of circulating immunocompetent cells such as lymphocytes. These cells otherwise have the potential to participate in an immune response, to lodge within the small capillaries and arterioles of the eye to form blockages and hence occlude blood flow, etc. In addition to lymphocytes, other hematopoietic cells may also be affected by immunotherapy, and include erythrocytes (red blood cells), megakaryocytes (precursors to platelets) and thrombocytes (platelets), and other leukocytes (white blood cells), such as monocytes and granulocytes. Local or in situ administration of immunosuppressant agents to the eye decreases the number of these cells. This results in reduction in the immune response, less blockage, increased blood flow, and increased patency of the ocular vessels.

Cyclosporin A in any of the previously described formulations, dosages, compositions, routes of administration, etc. may be employed. Because Cyclosporin A is injected or implanted directly in the eye, the undesirable effects brought about by administration of systemic therapy with Cyclosporin A (e.g., decreased peripheral blood leukocyte count, susceptibility to infections, hepatic and renal toxicity of the immunosuppressant agent itself, etc.) are absent. Cyclosporin A and related compounds may be administered by intraocular injection and/or intraocular implantation of a loaded capsule, microsphere, etc. (collectively termed an implant) to treat retinopathy, macular degeneration, and/or retinitis pigmentosa. The implant may release Cyclosporin A over a period of time, as previously described, so that high doses of drug can be loaded into the implant, but the patient will receive a low dose sustained concentration. That is, the matrix may be loaded or formulated so that it contains what would otherwise be a toxic or supratherapeutic amount of Cyclosporin A if the drug was released in a non-controlled manner.

It should be understood that the embodiments of the invention shown and described in the specification are only preferred embodiments of the inventor who is skilled in the art and are not limiting in any way. Therefore, various changes, modifications or alterations to these embodiments may be made or resorted to without departing from the spirit of the invention and the scope of the following claims.

The invention claimed is:

1. A method of treating diabetic retinopathy or retinitis pigmentosa in a patient in need thereof comprising intraocularly injecting a composition consisting essentially of Cyclosporin A in a pharmaceutically acceptable formulation and in an amount effective to treat diabetic retinopathy or retinitis pigmentosa without substantial toxicity to the patient.

2. The method of claim 1 comprising administering by retrobulbar, intravitreal, intraretinal, or subconjunctival injection.

3. The method of claim 1 wherein injection is subconjunctival at a dose in the range of about 1 ng/ml to about 500 µg/ml, intravitreal at a dose in the range of about 1 µg/0.1 ml to about 1000 µg/0.1 ml, retrobulbar at a dose in the range of about 20 µg/ml to about 1000 µg/ml, or subretinal at a dose in the range of about 1 µg/0.1 ml to about 100 µg/0.1 ml.

4. The method of claim 1 wherein Cyclosporin A is injected at a dose in the range of about 20 µg/ml to about 1000 µg/ml.

5. A method of treating diabetic retinopathy or retinitis pigmentosa in a patient in need thereof comprising intraocularly injecting a composition comprising Cyclosporin A in a pharmaceutically acceptable formulation and in an amount effective to treat diabetic retinopathy or retinitis pigmentosa without substantial toxicity to the patient.

6. The method of claim 5 comprising administering by retrobulbar, intravitreal, intraretinal, or subconjunctival injection.

7. The method of claim 5 wherein the composition further comprises an immunosuppressant selected from the group consisting of tacrolimus, cyclosphosphamide, sirolimus, atoposide, thiotepa, methotrexate, azathioprine, interferons, infliximab, etanercept, mycophenolate mofetil, 15-deoxyspergualin, thalidomide, glatiramer, leflunomide, vincristine, cytarabine, and combinations thereof.

8. The method of claim 1 wherein Cyclosporin A is provided in at least one of a microsphere, liposome, capsule or polymeric matrix.

9. The method of claim 5 wherein Cyclosporin A is provided in at least one of a microsphere, liposome, capsule or polymeric matrix.

10. A method of treating macular degeneration, diabetic retinopathy or retinitis pigmentosa in a patient in need thereof comprising intraocularly injecting a composition comprising Cyclosporin A in a pharmaceutically acceptable formulation and in an amount effective to treat macular degeneration, diabetic retinopathy, or retinitis pigmentosa without substantial toxicity to the patient, wherein injection is subconjuctival at a dose in the range of about 1 µg/ml to about 500 µg/ml, intravitreal at a dose in the range of about 1 µg/0.1 ml to about 1000 µg/0.1 ml, retrobulbar at a dose in the range of about 20 µg/ml to about 1000 µg/ml, or subretinal at a dose in the range of about 1 µg/0.1 ml to about 1000 µg/0.1 ml.

11. A method of treating macular degeneration, diabetic retinopathy or retinitis pigmentosa in a patient in need thereof comprising intraocularly injecting a composition comprising Cyclosporin A in a pharmaceutically acceptable formulation and in an amount effective to treat macular degeneration, diabetic retinopathy, or retinitis pigmentosa without substantial toxicity to the patient, wherein Cyclosporin A is injected at a dose in the range of about 20 µg/ml to about 1000 µg/ml.

* * * * *

UNITED STATES PATENT AND TRADEMARK OFFICE
CERTIFICATE OF CORRECTION

PATENT NO. : 7,354,574 B2  Page 1 of 1
APPLICATION NO. : 10/289772
DATED : April 8, 2008
INVENTOR(S) : Gholam A. Peyman It is certified that error appears in the above-identified patent and that said Letters Patent is hereby corrected as shown below:

Claim 10 - Col. 6, line 47 - 1 $\mu$g/ml should read: 1 ng/ml

Signed and Sealed this

Twenty-third Day of September, 2008

JON W. DUDAS
*Director of the United States Patent and Trademark Office*